United States Patent
Baust et al.

(10) Patent No.: US 8,409,184 B2
(45) Date of Patent: Apr. 2, 2013

(54) CRYO-MEDICAL INJECTION DEVICE AND METHOD OF USE

(75) Inventors: John M. Baust, Owego, NY (US); John G. Baust, Owego, NY (US); Anthony T. Robilotto, Binghamton, NY (US); Kristi K. Snyder, Candor, NY (US); Robert G. Van Buskirk, Apalachin, NY (US)

(73) Assignee: CPSI Holdings LLC, Owego, NY (US)

( * ) Notice: Subject to any disclaimer, the term of this patent is extended or adjusted under 35 U.S.C. 154(b) by 537 days.

(21) Appl. No.: 12/607,721

(22) Filed: Oct. 28, 2009

(65) Prior Publication Data

US 2011/0060323 A1   Mar. 10, 2011

Related U.S. Application Data

(60) Provisional application No. 61/240,863, filed on Sep. 9, 2009.

(51) Int. Cl.
*A61B 18/02* (2006.01)

(52) U.S. Cl. ............................ 606/21; 604/59; 604/61

(58) Field of Classification Search ............ 604/59–62; 606/20–22
See application file for complete search history.

(56) References Cited

U.S. PATENT DOCUMENTS

| | | | | |
|---|---|---|---|---|
| 1,653,353 A * | 12/1927 | Farmer | ............................ | 425/286 |
| 2,607,333 A * | 8/1952 | O'Dell | ............................ | 124/27 |
| 2,859,325 A * | 11/1958 | Lea | ............................ | 425/279 |
| 3,005,421 A * | 10/1961 | Lea | ............................ | 425/165 |
| 3,918,439 A * | 11/1975 | Zimmer | ............................ | 600/104 |
| 3,921,980 A * | 11/1975 | Artzer | ............................ | 273/405 |
| 4,077,406 A | 3/1978 | Sandhage et al. | | |
| 4,833,961 A * | 5/1989 | Adini | ............................ | 89/1.1 |
| 4,946,460 A * | 8/1990 | Merry et al. | ............................ | 606/24 |
| 4,976,686 A * | 12/1990 | Ball et al. | ............................ | 604/61 |
| 5,179,022 A * | 1/1993 | Sanford et al. | ............................ | 435/285.3 |
| 5,405,616 A | 4/1995 | Wunderlich et al. | | |
| 5,674,218 A | 10/1997 | Rubinsky et al. | | |
| 5,846,235 A | 12/1998 | Pasricha et al. | | |
| 6,041,787 A * | 3/2000 | Rubinsky | ............................ | 128/898 |
| 6,141,985 A * | 11/2000 | Cluzeau et al. | ............................ | 62/293 |
| 6,270,472 B1 * | 8/2001 | Antaki et al. | ............................ | 604/61 |

(Continued)

OTHER PUBLICATIONS

Fladerer et al. "Homogenous nucleation and droplet growth in supersaturated argon vapor: The cryogenic nucleation pulse chamber," Journal of Chemical Physics (2006), vol. 124. 2006 American Institute of Physics. USA.

*Primary Examiner* — Michael Peffley
*Assistant Examiner* — Jocelyn D Ram
(74) *Attorney, Agent, or Firm* — Melissa K. Dobson, Esq.

(57) ABSTRACT

The resorbable cryoprobe device and process is a novel approach for treating localized disease allowing for the precise combined application of freezing temperatures and cytotoxic or cryosensitizing agents within a self-contained matrix/package for optimized tissue destruction. The cryopellet is comprised of a list of components including a source of cryogen to produce the sub-zero temperatures, a porous matrix to contain the cytotoxic agent, cytotoxic agent, and a delivery packet. Data presented herein demonstrates the efficacy of this approach in destroying cancerous tissue. For example, the application of freezing temperatures to −10° C. results in approximately 15% cell death, while exposure to cytotoxic agents such as TRAIL produces minimal cell death. The utilization of the cryopellet approach results in a synergistic effect yielding complete cell death at the same temperature. The innovation behind the resorbable probe application includes the strategic combination of agents to activate intrinsic or extrinsic cell death responses (including apoptosis and necrosis), unique packaging of the cryogen and cytotoxic agent, and a unique delivery system. The resorbable cryoprobe technology will assist directly in the treatment of cancer, as well as will likely lead to broader application for disease treatment.

20 Claims, 5 Drawing Sheets

U.S. PATENT DOCUMENTS

| | | |
|---|---|---|
| 6,572,527 B2 | 6/2003 | Steele, Sr. et al. |
| 6,705,194 B2 * | 3/2004 | Geskin et al. ............... 89/1.1 |
| 6,726,693 B2 * | 4/2004 | Weber et al. ............... 606/131 |
| 7,306,589 B2 | 12/2007 | Swanson |
| 2004/0092920 A1 * | 5/2004 | Rozenshpeer ............... 606/22 |
| 2005/0214268 A1 | 9/2005 | Cavanagh, III et al. |
| 2006/0122588 A1 * | 6/2006 | Bischof et al. ............... 606/20 |
| 2006/0172014 A1 | 8/2006 | Curd et al. |
| 2006/0247578 A1 * | 11/2006 | Arguedas et al. ............. 604/181 |
| 2008/0027421 A1 | 1/2008 | Vancelette |
| 2008/0173028 A1 | 7/2008 | Littrup et al. |
| 2009/0011032 A1 | 1/2009 | Lepivert et al. |
| 2012/0016338 A1 * | 1/2012 | DiTrolio ............... 604/506 |

* cited by examiner

CRYO-MEDICAL INJECTION DEVICE AND METHOD OF USE

RELATED APPLICATIONS

The present application claims priority to U.S. Provisional Patent Application Ser. No. 61/240,863 filed on Sep. 9, 2009 and titled Cryosensitizing Agents for the Enhancement of Cryoablation, which is incorporated herein by reference.

FIELD OF THE INVENTION

The present invention relates generally to the medical technology field and, in particular, to a medical device and method for use in cryogenic treatments.

BACKGROUND OF THE INVENTION

Over a recent number of years, there has been a strong movement within the surgical community toward minimally invasive therapies. The main goals of the minimally invasive therapies include: 1) eradication of targeted tissue, 2) decreased hospitalization time, 3) limited postoperative morbidities, 4) shortened return interval to daily functions and work, and 5) reduced overall treatment cost.

Cryotherapy and cryosurgery (i.e. cryogenic treatments) are currently utilized for thousands of patients annually. The treatment provides a minimally invasive method of treating a disease state through tissue freezing as opposed to surgical treatment or radiation therapy. Numerous disease states include organ confined tumors such as prostate, kidney, liver, as well as cardiovascular disease, retinal detachment, pain management, and other illness/disease states such as cancer and cardiovascular disease.

Evidence demonstrates that standard therapies provide less than optimal efficacy in the treatment of prostate cancer (Moul, J., 1999; Van den Ouden et al., 1998). Prostate cancer (CaP) is the second leading cause of cancer-related death in men in the United States with more than 225,000 new cases diagnosed annually, approximately 40,000 resulting in death (Carter and Isaacs, 2004; Oh, 2000; Petrylak, 1999). CaP is often treated initially with androgen ablation. Unfortunately, androgen ablation is not curative in many patients and the disease recurs in later years. Subsequent to anti-androgen failure, radical prostatectomy and radiation therapy (external beam or brachytherapy) provide treatment options for localized prostate cancer. Additionally, there is often a high complication rate associated with these procedures characterized by high morbidity, long hospital/therapeutic intervals, incontinence, loss of potency, and additional adverse side effects. Given the high number of annual cases of CaP and the high recurrent rate, the appropriate resources need to be gathered to develop and improve primary and salvage treatment options.

Cryotherapy is an effective yet minimally invasive alternative to current surgical procedures and radiation therapy approaches. The surgical procedure is done under either general or epidural anesthesia and offers patients a quicker recovery and reduced severity of potential side effects. For example, cryogenic treatment of prostate cancer reduces or potentially eliminates side effects such as incontinence. Without the expense associated with major surgery or an extended hospital stay, cryosurgery is a cost-effective treatment option. The treatment is highly effective for low, moderate and high risk localized prostate cancers. Impotence, however, remains an expected side effect of targeted cryosurgery due to the freezing of tissue outside the gland to kill cancer cells that may have spread.

The approaches described thus far related to cryotherapy have focused around the development of devices which utilize stainless steel cryoprobes inserted into a target tissue, activation of a machine which circulates a cryogen (such as argon or liquid nitrogen) in the probe to create a heat sink thereby resulting in tissue freezing. Once freezing is complete, the probes are removed and the tissue left to die. None of the previous attempts have considered the nature of the cell/tissue death involved and the potential ways to manipulate the destruction of diseased tissue. In order to successfully reduce the positive freeze margin, methods or approaches are needed to elevate the critical killing temperature or cryosurgical "dose". The elevation of the critical kill temperature will not only apply to the freeze margin but also to specific locations within the tumor itself (i.e. neurovascular bundles). Targeting and enhancing specific cell death pathways involved with cryoablation through the combination of known cytotoxic agents can result in multiple cell stresses.

In addition, recent data demonstrate that when sub-lethal doses of cytotoxic agents applied in vitro, such as TNF-Related Apoptosis-Inducing Ligand (TRAIL), are applied in combination with freezing, complete prostate cancer cell death occurs. This enhanced cell death is in large part attained by the manipulation of the apoptotic, gene regulated, death cascade. Using this method, the critical death temperature has been reduced from $-40°$ C. to $-10°$ C.

The fundamental challenges faced by physicians using cryosurgery as a treatment for cancer revolve around the physics of the iceball produced, the surrounding anatomy, and the mechanisms of cellular destruction. Major anatomical structures, including the urethra, urinary bladder, rectal wall, and nerve bundles affecting erectile function, can be compromised during the procedure and result in secondary medical challenges to the patient (increased morbidity). To ensure complete ablation of the diseased tissue, however, physicians need to freeze a significant area beyond the disease margin. Many improvements have been made including monitoring of the freeze zone advancement and the use of a urethral warming device. While the warming device has led to a decreased incidence of incontinence, this device may impede cellular destruction within the tumor near the urethra.

The nature of cryosurgery generally requires a temperature of $-40°$ C. or colder to ensure complete cell and tissue destruction. In order to achieve this "dose" during a typical cryosurgical procedure, the ice front or positive freeze margin should extend from 2-5 mm beyond the targeted tissue. This necessary positive freeze margin leads to significant damage to adjacent healthy tissue and unwanted patient side-effects. A variety of approaches have been developed in an attempt to minimize the freeze margin. Some of these include a change in the design of the probe resulting in different sized iceballs, an increase in the number of probes used for each procedure to produce a more uniform iceball, and multiple freeze-thaw cycles. While each of these techniques has led to some improvement in the efficacy of the procedure, none of them have been successful at completely negating the need to extend the freeze zone. Some of the major drawbacks include the physics of the ice formation and the isotherms generated, individuality amongst patients, and differences between physician applications, all of which lead to inconsistent results.

There exists a need for improvements in cryotherapy, and medical devices or components associated with the treatment to better facilitate and improve measures for treatment and cost. Studies are necessary to demonstrate that combining therapeutic strategies can increase the efficacy compared to each as a single agent. The combination of various chemotherapeutic agents includes potential benefits of combining classical cryosurgery and chemotherapy. The use of adjuvant methods has the potential to significantly reduce the need to extend the freeze margin while attaining enhanced efficacy. Having the ability to target specific sites within or around the tumor will help to protect those areas not intended to be destroyed.

As cryosurgery continues to gain acceptance, future improvements to the design and application will be desired to significantly improve its usage in prostate cancer as well as for the treatment of multiple other types of organ-confined tumors. While present treatments typically use cryosurgery as the sole therapy or as a single procedure, innovation and future developments will recognize the benefits of combination (neoadjunctive) therapies, including various therapeutic benefits in the control and eradication of cancerous tumors.

The medical device and methods of the present invention will allow for the simultaneous application of cryotherapy and cytotoxic agent therapy in a novel delivery system. The invention will desirably allow for the insertion of single or multiple delivery systems to produce a destructive treatment and/or freeze zone. Further, the invention will provide for a resorbable system or probe to more specifically target the designated tissue. The invention will facilitate the ablation or eradication of tissue, decrease procedural related side effects, increase therapeutic efficacy, decrease hospitalization time, limit postoperative morbidities, shorten return to daily functions and work, and further reduce the overall treatment cost. Desirably, these improvements to device design and application will also increase its utilization for the treatment of multiple disease states.

SUMMARY OF THE INVENTION

The resorbable probe approach offers the unique ability for the simultaneous application of cryotherapy and cytotoxic agent therapy in a novel delivery system or contained packet. The resorbable probe or cryopellet approach allows for the insertion of multiple (single to hundreds) pellets to the target tissue to produce a destructive treatment/freeze zone. The resorbable probe or resorbable cryopellet technology also decreases procedural related side effects, increases therapeutic efficacy, and reduces overall cost, ultimately leading to increased cryosurgical application to numerous other disease states.

The following invention is a medical injection device comprising one or more treatment pellets, an injection assembly which has a mechanism for discharging the pellets, and a cartridge providing storage for the treatment pellets and supplying pellets to the injection assembly. An insertion needle has a proximal end and a distal end such that the distal end of the insertion needle designates at least one dispensing site, or situs (defined region within tissue), for placement of one or more of the treatment pellets into a targeted tissue.

In one embodiment, the medical injection device may be an insertion needle with a cavity formed therethrough or the insertion needle may serve more as a catheter or probe in an integral injection assembly such that a sleeve and plunger apparatus provide a mechanical force to dispense a donut-shaped pellet from a storage cartridge into the target tissue.

In another embodiment, the injection assembly is a cryogun which fires a injectable substrate or cryopellet into a target tissue. Alternatively, the cryogun may serve as an injection device to pre-treat the target tissue with an adjuvant prior to cryotreatment. In one aspect, the treatment pellets comprise a porous matrix. In another aspect, the treatment pellets are a cryo-formulation solidified and designed for resorption into the target tissue.

In one embodiment of the invention, an injectable substrate is used in the treatment of the target tissue. The injectable substrate has a rigid or semi-rigid configuration for mechanical discharge into a target tissue site for use in the treatment of a target tissue, such that the injectable substrate comprises a matrix which has a resorbable composition within a water soluble hydrophilic environment, and such that the matrix is an emulsion, gel, paste, liquid, or particulate form. Aspects of the injectable substrate may include a porous matrix having varying porosities. Various aspects of the substrate may incorporate any number of additives, binder materials, fillers, or tissue engineered matrices. The porosity of the matrices may also vary as dependent on the materials and substrate compositions utilized.

In another embodiment, a method of using the device of the present invention is disclosed. The method of injecting one or more treatment pellets or resorbable probes into a target tissue comprises the steps of: providing a medical injection device having a storage unit, an injection needle, and one or more treatment pellets; targeting a tissue to be treated; inserting the injection needle into the tissue at a defined site for treatment; and injecting one or more treatment pellets into a defined tissue site. In one aspect, the method includes determining an effective treatment plan for treating the tissue at one or more defined sites within the tissue. In another aspect, the treatment pellets are designed as resorbable cryoprobes and are capable of providing adjuvant therapy means to the tissue site.

In embodiments of the present invention, a cryopellet or cryoprobe technology is utilized for the improved and successful ablation of localized (targeted) tissue in cancerous and benign tissues, noncancerous tissue, and irregular or non-conforming tissue structures. The cryopellet accomplishes this through utilization of the destructive force of freezing combined with specific cytotoxic agents in a delivery packet which is applied to the diseased tissue using a uniquely designed delivery system. Aspects of the inventive cryopellet are disclosed such that the cryopellet may be composed of a porous matrix, resorbable or non-resorbable, in a frozen or non-frozen state, with or without a cytotoxic agent (including but not limited to TRAIL, taxotere, cisplatin, etoposide, 5-FU, etc.), and delivering a time-released dosage of temperature and/or cytotoxic agent. The cryopellet can be delivered as a stand alone pellet or in conjunction with a cryoprobe as currently used in the art to destroy target tissue. Furthermore, the concept allows for the site-specific targeting of diseased tissue by facilitating more precise delivery of a therapeutic dose to the desired location. The cryopellet can be applied in either a frozen pellet formation or simultaneous injection of a non-frozen packet and in conjunction with a cryoprobe for site-specific tissue ablation.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

The resorbable probe device and approach to treat cancer, other bulky diseased, irregular, or undesired tissue(s), represents an important step in targeted therapies. Numerous studies have been published detailing various cryosurgical devices and procedures to apply freezing temperatures to a target tissue. To date though, no reports detailing an approach similar to a cryopellet or a resorbable probe approach to ablate tissue have been disclosed. Furthermore, no device or delivery method has been developed to administer combined agents as do the treatment pellets within the tissue or tumor site.

Figure 1:
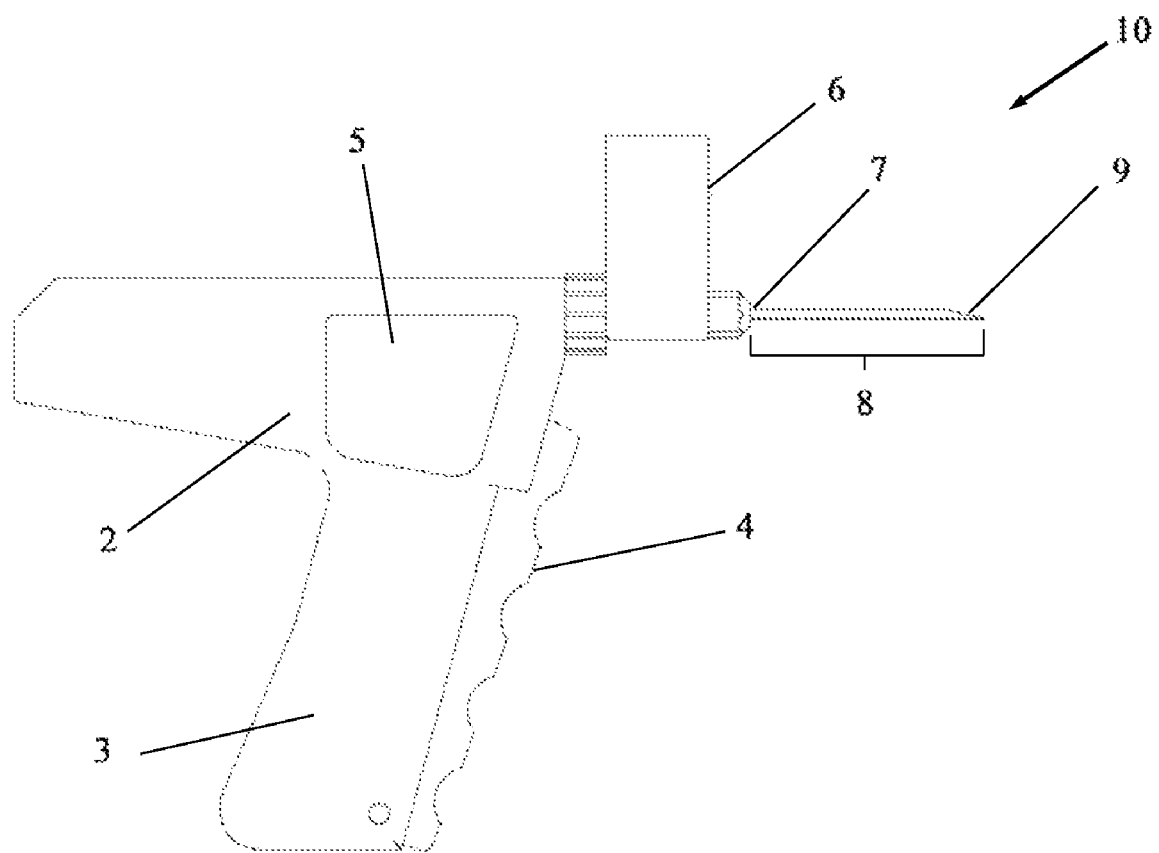
FIG. 1 is a side view of an illustrative embodiment of a device of the present invention.

A device of the present invention is a medical injection device 10 as represented in FIG. 1. The injection device 10 has a cryogun configuration such that the body 2 of the cryogun 10 includes a handle 3 and finger-grip trigger 4. The storage clip or cartridge 6 holds the treatment pellets (see FIG. 2) to be dispensed. An insertion needle 8 includes a proximal end 7 and a distal end 9.

In the embodiment of FIG. 1, the needle 8 has a cavity formed through it that runs the length of the needle 8. An access panel 5 allows access to the internal mechanism that facilitates discharge of the treatment pellet(s) to the distal end of the needle at a tissue site. Upon discharge of the pellet, the pellet is directed from the storage cartridge 6 into and through the needle 8 to a target tissue. The placement of the distal end 9 of the insertion needle 8 designates the dispensing situs (or tissue site) where individual or multiple treatment pellets are released into the tissue.

In one embodiment of FIG. 1, the needle can puncture tissue and be placed as near to the target as possible. In one aspect, the needle can have a diameter of any size and shape. The needle 8 may further contain extensions to reach a more internal tissue or organ within the patient being treated. In another aspect, the needle is an integral unit of multiple lengths. On the other hand, the needle may contain distinct fragment lengths that are interconnected and disposable.

It should be noted that current methods utilize a mechanical discharge method though an air compression mechanism or other means for projecting the pellet down the needle may be utilized.

As depicted in the embodiment of FIG. 1, the injection assembly 2 is the body 2 of the cryogun and has a mechanism for discharging cryopellets to a target tissue. The storage clip 6 supplies the injection assembly with the cryopellets and has a means for maintaining sub-zero temperatures. A cooling means or cooling mechanism may be integrated with the storage clip itself or with any portion of the cryogenic treatment device 10. The cooling mechanism keeps the cryopellets in a solidified state prior to release into the patient. Further, the insertion needle may be rigid or flexible to directionally place the cryopellets into the target tissue at its distal end. The needle itself can direct where the cryopellets are released.

In one aspect, the cryogenic treatment device 10 is connected to a cryogen source. The cryogen source may be a fluid, including gases and liquids. For example, and not limitation, the cryogen source may include argon, nitrogen, nitrous oxide, helium, freon, and other cryogenic gas, used individually, in combination, or in any mixtures thereof. In another aspect, cryogenic fluid can be directed to the storage clip where cryopellets are molded and formed prior to discharge. This would maintain consistency of pellet size in the device utilized or allow for selected pellet size designs per each cartridge or per each cryogun design.

Another embodiment may incorporate a cryopellet supply which has a direct feed into the storage clip. Then, the cryogenic treatment device has freedom of use anywhere in the patient setting without direct attachment to a cryogen source.

Figure 2:
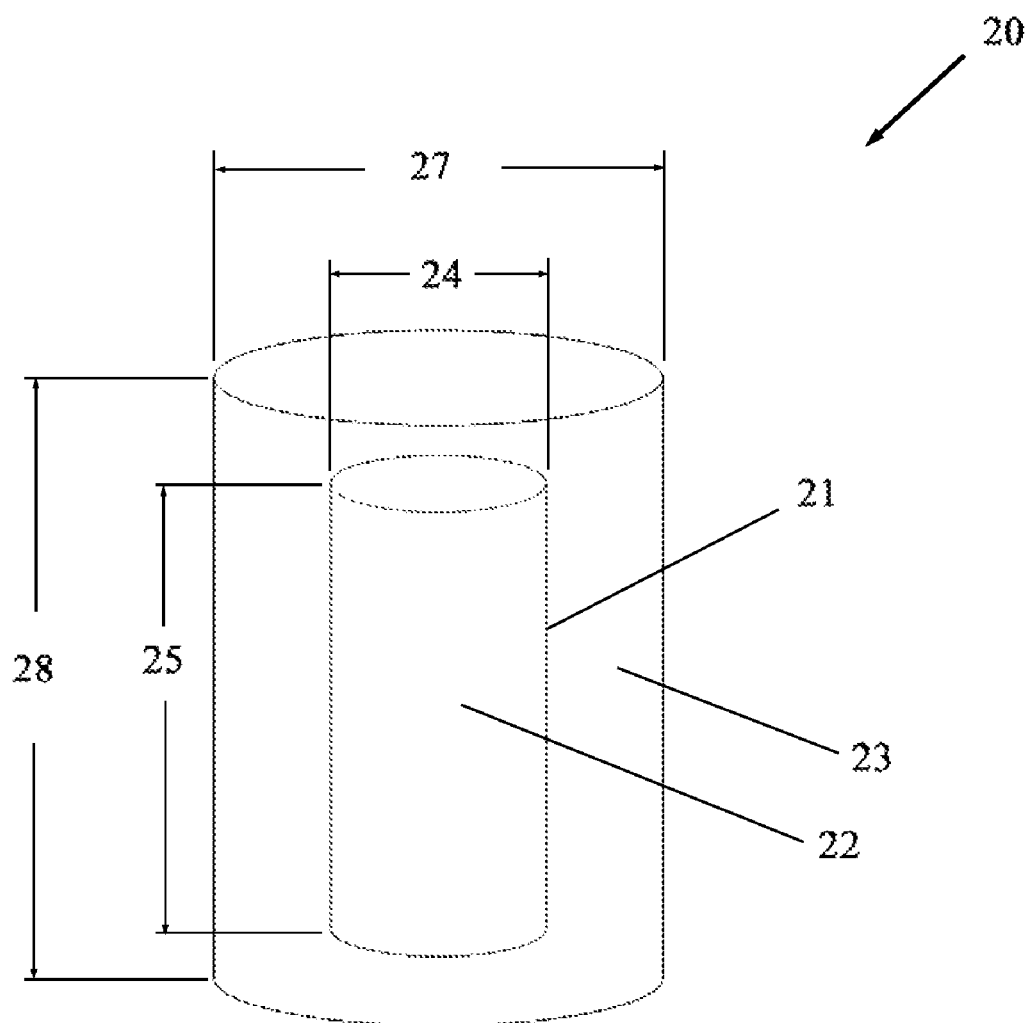
FIG. 2 is an illustrative embodiment of a device of the present invention.

FIG. 2 illustrates an injectable substrate 20 of the present invention. The injectable substrate 20 comprises a porous matrix 22 with a resorbable composition within a water soluble hydrophilic environment (although other porous matrices may be utilized such as for organic solubility). The outer wall 21 of the substrate 20 is typically rigid or semi-rigid for mechanical discharge into a target tissue site. The matrix can be an emulsion, gel, paste, liquid, or particulate form in similar configuration to that of an orally dissolvable capsule. In another aspect, the matrix may be an engineered synthetic or natural formulation for supporting the compositions within an integral unit or as a unitary article.

The diameter of the pellet is typically between about 1 mm-10 mm, preferably between about 5 mm-10 mm, but may even be desired to be in the range of about 1 mm-2 mm or smaller. The pellet size may be any size that facilitates ease of use of the medical injection device such that the pellet 20 is configured to fit within the storage clip and discharge through the distal end of the needle into the target tissue. Aspects of the injectable substrate, however, may include a porous matrix having varying porosities of any size and any dimension.

The length of the pellet may also extend between about 5 mm up to about 20 mm in length. Again, the pellet is designed to facilitate ease of use of the medical device, but the pellet may also be engineered as to the type of tissue being treated, including size and position of the tissue site. Any dimension of pellet, however, is capable of formation but development of the pellet provides a design that also takes into account the tissue treatment plan, disease state of the tissue and other patient care factors.

In addition, the pellet may be utilized in current brachytherapy systems and methodologies. Making pellet diameters in the range of about 0.1 mm-3 mm may be preferable. Lengths could vary in the same dimension or larger. Actual dimensions and surface area can vary to achieve the desired ablation volume or treatment area. Complete pellet sizes smaller, in the range of about 0.1 mm-0.9 mm may also satisfy minimally invasive therapeutic methodologies.

In FIG. 2, a cryopellet 20 is depicted having a diameter 24 of about 5 mm with a length 25 of about 20 mm. The produced freeze zone diameter 27 created is therefore up to about 15 mm. The produced freeze zone length 28 is about 25 mm. As demonstrated, the cryopellet 20 has an extended area of treatment 23 predetermined by its design size, shape, and configuration. When the matrix of the treatment pellet is altered, the extended zones of treatment vary as dependent on the selected substrate material 22.

Figure 3:
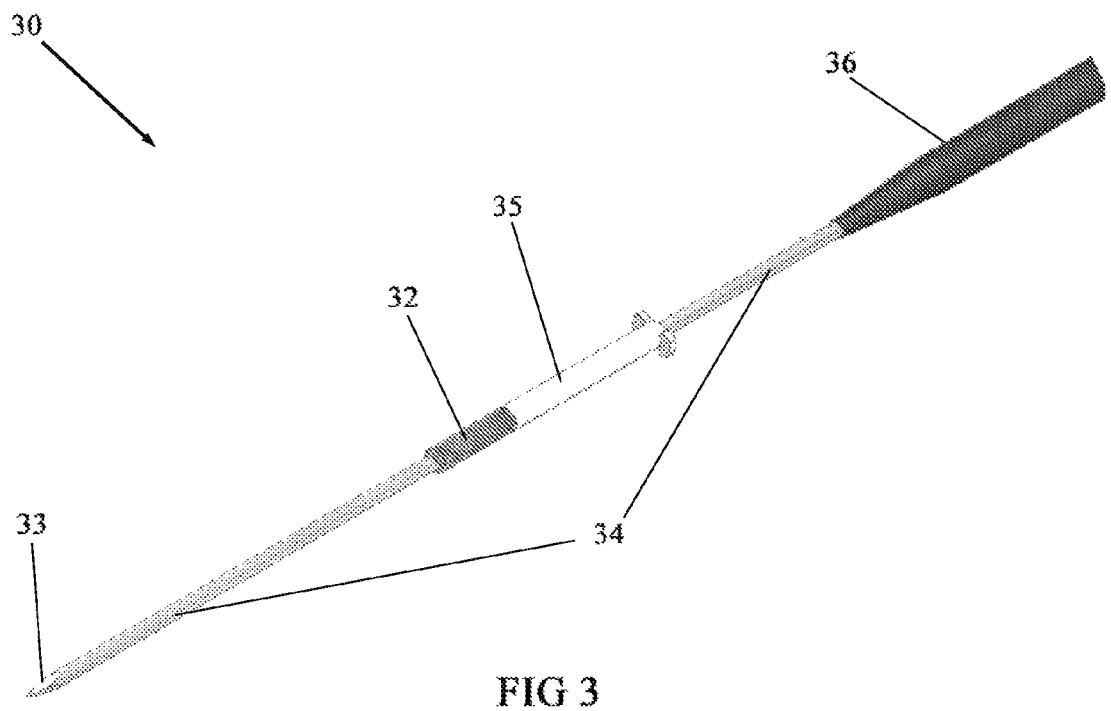
FIG. 3 is an illustrative embodiment of a device of the present invention.

Another embodiment of the invention is depicted in FIG. 3 as a medical injection device 30 having a packet or cartridge 32 which houses one or more treatment pellets (see FIG. 5) or embodies a uniform treatment packet 32 for injection into a designated tissue site. The cartridge 32 depicted here has a hollow core that is wrapped around the needle 34. The injection device 30 in this embodiment integrates the concept of a catheter/probe 34 which serves as the needle 34. As depicted, the needle tip probe 34 is connected with a hose 36 which extends from a cryogenic console (not illustrated). An injection assembly/plunger 35 wraps itself around the needle 34, behind the cartridge 32 and pushes the cartridge/packet 32 over the catheter tip 33 and into the tissue where the tip of the needle is situated.

In one aspect, the injection device 30 is an injection guide 30 which is utilized in conjunction with a standard cryoprobe for the guided placement of the cryopellet into the targeted tissue. However, the novelty of the invention as to the dispensable and resorbable cryoprobe pellet can be varied to accommodate any cryo-instrumentation for the various surgical and/or cryotherapeutic procedures.

Figure 4:
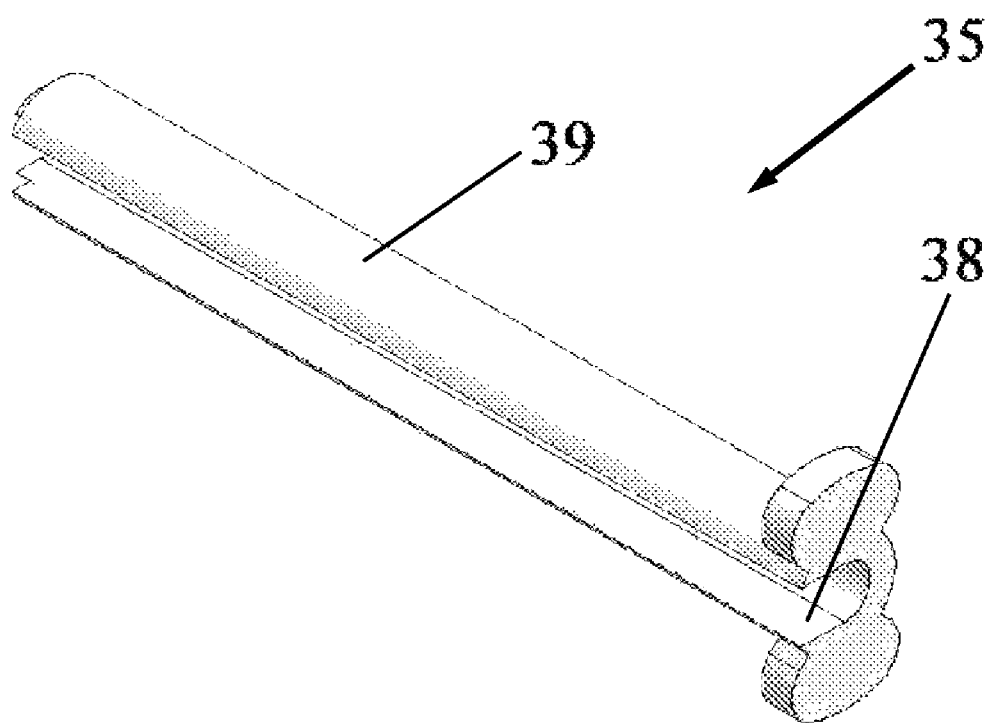
FIG. 4 is a perspective view of the plunger described in the device of FIG. 3.

It is noted, however, that the needle-like probe may also be a needle-tip catheter of any design or configuration. The pellet configuration may also be modified to conform to the medical injection device design. A more detailed perspective view of the injection assembly, or plunger 35, is depicted in FIG. 4. A hollow space 38 is internal to the outer wall 39 and can be configured to integrally connect with the catheter/probe 34 of the injection device 30.

Figure 5:
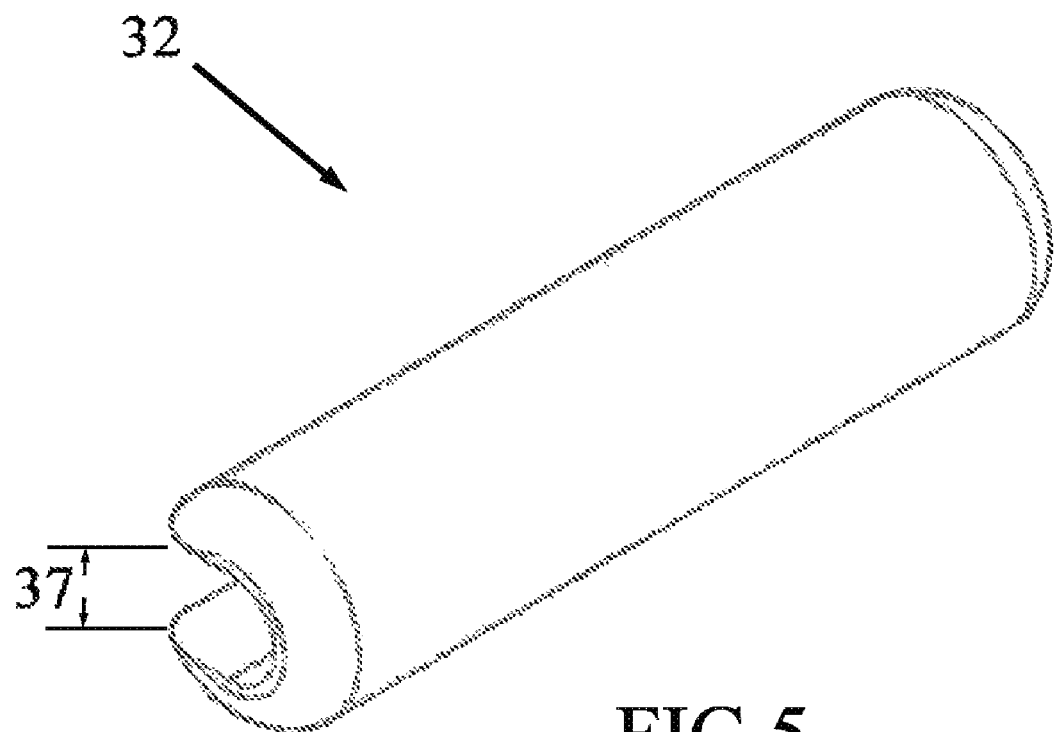
FIG. 5 is a perspective view of a packet as described in the device of FIG. 3.

The treatment packet 32, as illustrated in FIG. 5, is a resorbable probe 32. For exemplary purposes only and not limitation, the illustration of FIG. 5 depicts a resorbable pellet 32 having a hollow core 37 to be discharged over the surface of the catheter or probe tip 33. The dimensions, size, shape and configuration of both plunger and treatment packet(s) can be modified to suit the type of tissue being treated. Further, the internal diameter of the hollow space 38 of the injection assembly 35, as well as the internal diameter of the hollow core 37 of the resorbable pellet 32 may be similarly constructed for optimal performance of the injection assembly. When one or more pellets 32 are utilized for treatment, the injection assembly 35 can controllably release each pellet individually or in numerous quantities simultaneously. Insertion of the treatment pellets may be manual under the user's direction or automated based on a desired treatment plan. Such treatment measures would permit consistency and accuracy in treatment procedure methods and less dependent on the user. A user interface, however, allows easy control and manipulation of the injection device, including precise mechanisms and electronic controls for ease of use.

More specifically, in the CryoPellet™ approach, a frozen pellet or packet is inserted into the target tissue, freezes the adjacent tissue, and is left in place following application. The cryopellet can be composed of either a resorbable or non-resorbable porous scaffold (liquid, semisolid, or solid) which is solidified or frozen to a desired temperature (typically ranging from −20° C. to −196° C.) prior to injection. The cryopellet may also be impregnated with a single or multiple cytotoxic agents including, but not limited to, TRAIL, docetaxel (Taxotere®), Cisplatin, etoposide, 5-Flurouricil (5-FU), paclitaxel (Taxol®), and other ligands and/or apoptotic drugs at clinical or sub-clinical doses. In addition, the composition of the porous matrix may be comprised of any biocompatible material, water, dimethyl sulfoxide (DMSO), ethanol, and including any cryosensitizing agent or cytotoxic agent dissolvable or suspendable in the selected medium. Other cryosensitizing agents as utilized may include vitamin $D_3$ and other analogs. The selected medium creates a fluid-based (i.e. water-containing or liquid based) pellet in either liquid or solid form. For exemplary purposes and not limitation, any biologic or chemotherapeutic compound could be utilized or incorporated within the porous matrix to achieve a desired therapeutic outcome.

One example of a cryopellet configuration is a frozen carbon dioxide pellet (−79° C.) impregnated with the cytotoxic agent TRAIL. Another example configuration is an aqueous solution of Taxotere® frozen to a temperature of −196° C. When injected, these cryopellets create mini ice balls within the target which destroys the surrounding tissue. In the case of cryopellets containing cytotoxic agents, the combination of an agent and freezing act in conjunction with one another in a time dependent manner to destroy the target tissue. The frozen state of the cryopellet, with or without a cytotoxic agent delivers a time-released dosage of temperature and/or cytotoxic agent (if present).

In another configuration of the cryopellet, a non-frozen pellet (encapsulated liquid, semi-solid, or solid) is injected into the target tissue and is then frozen in situ utilizing the cooling power of a cryoprobe. The agents with the pre-frozen configuration, non-frozen pellets, may consist of resorbable or non-resorbable porous scaffolds and/or a single cryoagent or combination of cytotoxic agents.

These cryopellets can be best equated to the radioactive seeds utilized in brachytherapy; however, in the case of the cryopellets, the low temperature nature of the pellet destroys the tissue where as in brachytherapy, a piece of radioactive material is inserted into a tissue in attempt to kill the surrounding tissue over many weeks to months.

The innovation of this approach is that the cryopellet system offers a novel concept, approach, device and method for the treatment of cancer. The cryopellet system through its unique flexible design is the first self-contained cryosurgical device and approach which can be utilized as a stand-alone therapy (in various configurations) or in conjunction with existing cryosurgical devices. Utilization of the CryoPellet™ system has the potential to revolutionize the way cancer is treated through further reducing the invasive nature of cancer therapy procedures while providing for a highly effective approach to treating cancer.

In utilizing the medical device of the present invention, various methods in the industry may be employed in accordance with accepted cryogenic applications. As discussed, the embodiments of the present invention are for exemplary purposes only and not limitation. Advantageously, this device represents an important step in targeted thermal therapies. Various cryosurgical devices and procedures to apply freezing temperatures to a target tissue may be employed for use with the medical device of the present invention. The medical device of the present invention has been developed to enable and improve some of the approaches used to target or ablate tissue.

Thus, the invention facilitates other improvements in cryotherapy, and medical devices or components associated with the treatment. The invention facilitates the eradication of tissue and can thereby decrease hospitalization time, limit postoperative morbidities, shorten return to daily functions and work, and further reduce the overall treatment costs. These improvements to device design and application can also increase utilization of the device for the treatment of multiple disease states.

The embodiments of the present invention may be modified to take the shape of any device, container, apparatus, or vessel currently used in industry. Further, any compartmental arrangement in combination with the components of the above system may take many forms and be of any size, shape, or passageway. Any number of probes may also be utilized to facilitate various treatment plans as determined by the patient. In addition, the device and instrumentation of the present invention may integrate a user interface of mechanical and/or electrical components for facilitation of use in the medical setting. The user interface would preferentially be easy to use and easy to control the internal injection system and interoperability of the medical device and its injectable substrate.

As presented, the multiple embodiments of the present invention offer several improvements over standard medical devices currently used in cryogenic industry. The previously unforeseen benefits have been realized and conveniently offer advantages for the treatment of multiple disease states. In addition, the improvements enable construction of the device as designed to enable easy handling, storage, and accessibility. Further uses of the system outside of the healthcare setting are foreseeable. Potential uses in the space industry, defense systems or any industry requiring rapid cooling may incorporate the cryogenic system as thus described.

As exemplified, the device may include any unitary structure or integral configuration with the capacity to integrally incorporate any combination of such structures. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

What is claimed is:

1. A medical injection device comprising:
   one or more cryotreatment pellets solidified between about −40° C. and about −196° C. to deliver an ablative dosage of temperature within a target tissue, each of said one or more cryotreatment pellets configured as a uniform treatment packet;
   an injection assembly having a gas compression mechanism or mechanical plunger to guide placement of said one or more cryotreatment pellets;
   a cartridge providing storage of said one or more cryotreatment pellets and supplying said injection assembly with said one or more cryotreatment pellets; and
   an insertion needle having a proximal end and a distal end; wherein said distal end of said insertion needle is adapted to puncture a target tissue and to be positioned within at least one dispensing site of said target tissue to guide placement of said one or more cryotreatment pellets.

2. The medical injection device of claim 1, wherein said insertion needle comprises a cavity formed therethrough between said proximal end and said distal end.

3. The medical injection device of claim 1, wherein said insertion needle integrates said injection assembly with a catheter or probe.

4. The medical injection device of claim 1, wherein said insertion needle comprises a sleeve and plunger apparatus for dispensing said one or more treatment pellets.

5. The medical injection device of claim 1, wherein said one or more cryotreatment pellets is a porous matrix.

6. The medical injection device of claim 1, wherein said one or more cryotreatment pellets comprises a formulation which solidifies upon freezing to between about −79° C. to about −196° C.

7. The medical injection device of claim 6, wherein said formulation comprises vitamin $D_3$ and vitamin $D_3$ analogs.

8. The medical injection device of claim 1, wherein said one or more cryotreatment pellets comprises thermophysical adjuvants, chemotherapeutic molecules, cytokines, vascular-based agents, immunomodulators, apoptotic agents, vitamins, free radical scavengers, alone or any combination thereof.

9. The medical injection device of claim 1, further comprising a user interface having electronic control.

10. A cryogenic treatment device comprising:
    an injection assembly to guide placement of one or more cryopellets to a dispensing situs within a targeted tissue;
    a storage clip supplying said injection assembly with said one or more cryopellets and having a cryogen source which supercools a cryopellet between about −40° C. and about 196° C. prior to injection; and
    an insertion needle having a proximal end and a distal end wherein said distal end is adapted to puncture said targeted tissue and to extend directly to said dispensing situs within said targeted tissue to direct said one or more cryopellets.

11. The cryogenic treatment device of claim 10, wherein said cryogen source is a cryopellet supply having a direct feed into said storage clip.

12. The cryogenic treatment device of claim 10, wherein said cryogen source is argon, nitrogen, nitrous oxide, helium, freon, other cryogenic gas, or mixture thereof.

13. The cryogenic treatment device of claim 10, wherein said cryogen source is directed to said storage clip.

14. The cryogenic treatment device of claim 10, wherein said one or more cryopellets is formed within said storage clip.

15. The cryogenic treatment device of claim 10, wherein said distal end of said insertion needle has a cavity formed therethrough and is adapted to directionally position said one or more cryopellets within said targeted tissue.

16. A method of injecting one or more treatment pellets into a target tissue, said method comprising the steps of:
    providing the medical injection device of claim 1;
    targeting a tissue to be treated;
    inserting said insertion needle into said tissue at the at least one dispensing site for treatment; and
    injecting said one or more cryotreatment pellets into said at least one dispensing site.

17. The method of claim 16, further comprising the step of selecting a size for said one or more treatment pellets.

18. The method of claim 16, further comprising the step of determining an effective treatment plan for treating said tissue at one or more of said defined sites.

19. The method of claim 16, further comprising a step of cooling said one or more treatment pellets to sub-zero temperatures when said treatment pellets are cryoprobes.

20. The medical injection device of claim 1, wherein said insertion needle is solid and said one or more cryotreatment pellets are donut-shaped and are formed around said proximal end of said insertion needle and pushed over an external surface of the needle to said distal end for injection into said target tissue.

* * * * *